United States Patent
Panin

(10) Patent No.: US 10,406,193 B2
(45) Date of Patent: Sep. 10, 2019

(54) COMPOSITION FOR TOPICAL APPLICATION WITH ANTIFUNGAL ACTIVITY

(71) Applicant: BIO.LO.GA. S.R.L., Conegliano (TV) (IT)

(72) Inventor: Giorgio Panin, Rovigo (IT)

(73) Assignee: BIO.LO.GA. S.R.L., Conegliano (TV) (IT)

(*) Notice: Subject to any disclaimer, the term of this patent is extended or adjusted under 35 U.S.C. 154(b) by 0 days.

(21) Appl. No.: 16/326,562

(22) PCT Filed: Oct. 20, 2017

(86) PCT No.: PCT/EP2017/076807
§ 371 (c)(1),
(2) Date: Feb. 19, 2019

(87) PCT Pub. No.: WO2018/077733
PCT Pub. Date: May 3, 2018

(65) Prior Publication Data
US 2019/0224263 A1    Jul. 25, 2019

(30) Foreign Application Priority Data

Oct. 28, 2016 (IT) .................. 102016000109403

(51) Int. Cl.
| | |
|---|---|
| *A61K 36/00* | (2006.01) |
| *A61K 36/61* | (2006.01) |
| *A61K 9/00* | (2006.01) |
| *A61K 36/53* | (2006.01) |
| *A61P 31/10* | (2006.01) |
| *A61K 31/355* | (2006.01) |
| *A61K 9/06* | (2006.01) |
| *A61K 36/752* | (2006.01) |

(52) U.S. Cl.
CPC ............ *A61K 36/61* (2013.01); *A61K 9/0014* (2013.01); *A61K 9/06* (2013.01); *A61K 31/355* (2013.01); *A61K 36/53* (2013.01); *A61K 36/752* (2013.01); *A61P 31/10* (2018.01)

(58) Field of Classification Search
CPC .................................................. A61K 36/00

USPC ........................................................ 424/725
See application file for complete search history.

(56) References Cited

U.S. PATENT DOCUMENTS

| | | | |
|---|---|---|---|
| 6,413,555 | B1 | 7/2002 | Lee |
| 6,680,074 | B1 | 1/2004 | Morice |
| 2004/0151710 | A1 | 8/2004 | Bozzacco |
| 2009/0186096 | A1 | 7/2009 | Kritzman et al. |
| 2014/0242138 | A1* | 8/2014 | Kritzman ............... C11D 3/505 |
| | | | 424/408 |

FOREIGN PATENT DOCUMENTS

| | | |
|---|---|---|
| KR | 10-0285781 | 1/2001 |
| WO | 9637210 A2 | 11/1996 |
| WO | 2015144583 A1 | 10/2015 |
| WO | 2016051403 A1 | 4/2016 |

OTHER PUBLICATIONS

International Search Report and Written Opinion for Corresponding International Appiication No. PCT/EP2017/076807 ( 10 Pages) (dated Feb. 8, 2018).

* cited by examiner

*Primary Examiner* — Michael V Meller
(74) *Attorney, Agent, or Firm* — Lucas & Mercanti, LLP

(57) ABSTRACT

A composition for topical application with antifungal activity, containing *Melaleuca alternifolia* essential oil, oregano essential oil, lime essential oil and an ester of vitamin E is enclosed. Vitamin E acetate, n-propionate or linoleate, and is preferably alpha-tocopheryl acetate; preferably, these oils constitute at least 3% by weight of the composition and each of them constitutes at least 1% by weight of the composition; preferably, the composition contains from 10% to 97% of the ester of vitamin E and can consist of the three aforementioned essential oils and the vitamin E ester; alternatively, the composition can be in the form of hydrophobic gel, containing 10 to 50% of the ester of vitamin E, 20 to 60% of a vegetable butter or wax, from 10 to 30% of triglyceride of caprylic and capric acid and from 5 to 20% of a gelling agent for lipids and at least 3% of the aforementioned essential oils, each of which constitutes at least 1% by weight of the composition.

11 Claims, No Drawings

COMPOSITION FOR TOPICAL APPLICATION WITH ANTIFUNGAL ACTIVITY

CROSS-REFERENCE TO RELATED APPLICATIONS

This application is a 371 of PCT/EP2017/076807, filed Oct. 20, 2017, which claims the benefit of Italian Patent Application No. 102016000109403, filed Oct. 28, 2016.

TECHNICAL FIELD

The present invention refers to the field of the pharmaceutical and the cosmetics industry.

In particular, the invention refers to a composition for topical application for the prevention and the treatment of skin mycoses.

BACKGROUND ART

Mycoses are infections caused by fungi, which comprise different groups of microorganisms—among which are dermatophytes—yeasts, molds etc., which can infect the skin (dermatophytoses), the hair (tinea), the nails (onychomycosis) and the genital areas (e.g. infections caused by *Candida albicans*).

Dermatophytes are fungi that need keratin to develop and that cause the formation of distinctive rosette-like maculae on the skin. Some dermatophytes can infect the scalp (tinea captis), the face (tinea faciei), the hands (tinea manuum), the torso (tinea corporis), the nails (tinea unguium) and the feet (tinea pedis or athlete's foot).

The yeasts (e.g. *Candida albicans*) are instead located in the warm and humid areas (oral cavity, armpits, interdigital spaces, genitalia). In particular, *Candida Albicans* can cause diseases at the corners of the mouth, the lips (cheilitis), the oral cavity (thrush), male and female genitalia and the nails.

The diagnosis of the mycoses avails itself of investigations by microscopy and/or culturings on biological material collected from the affected areas to detect the type of fungus responsible for the infection and select the most adequate antifungal therapy to treat such fungus.

Sometimes, the diagnosis process is not easy, also because the infections may be due to a plurality of fungi that can have different characteristics of sensitivity/resistance with respect to a given antifungal agent.

Consequently, topical treatment therapies performed with the conventional antifungal agents (e.g. econazole, fluconazole, ketoconazole, griseofulvin, amorolfine) can occasionally be not completely effective.

It is therefore desirable to have at disposal a therapeutic agent for the topical treatment of mycosis that presents a broad spectrum of action and that can be used with the highest safety.

In this regard, the antifungal effect of the *Melaleuca Alternifolia* (tea tree) extract is known since a long time and has been described for example by Nenoff P. et al. in Skin Pharmacol. 1996; 9(6):388-94.

The use of a liquid composition comprising the essential oils of tea tree (*Melaleuca Alternifolia*), lavender and *eucalyptus* for the treatment of onychomycosis is known from U.S. Pat. No. 6,413,555 too.

Moreover, the use of the oregano essential oil for the treatment of onychomycosis is known from WO 9637210.

KR 100285781 describes a composition with antifungal and antimicrobial activity containing oregano oil and another essential oil, which can be, among the others, tea tree oil.

A method for the treatment of a tissue affected by an infection caused by bacterial, fungal or viral pathogenic organisms, comprising the topical application of a composition comprising tea tree oil, an immunostimulant, typically coenzyme Q, and an antioxidant, typically vitamin E is known from the application US 2004/151710. In the description of this application it is stated that the antimicrobial action is due to the tea tree oil, while the coenzyme Q reinforces the immune response of the infected tissue and the antioxidant scavenges the free radicals in the infected tissue, thus contributing to the inhibition of the damage caused by the free radicals.

The antifungal activity of the lime essential oil towards several strains of fungi is reported in the article of Tagoe D. et al. "A Comparison of The Antimicrobial (Antifungal) Properties Of Garlic, Ginger And Lime On *Aspergillus Flavus, Aspergillus Niger* And *Cladosporium Herbarum* Using Organic And Water Base Extraction Methods", The Internet Journal of Tropical Medicine, Vol. 7, No. 1.

WO 2015/144583 discloses a formulation for personal hygiene in the form of a O/W emulsion with a pH from 5.5 to 6.5, free of surfactants, comprising an emulsifier consisting of a fatty alcohol from 14 to 22 carbon atoms or of Glyceryl Stearate or a mixture thereof, Coco Caprylate and/or Coco Caprylate/Caprate, vitamin E or an ester thereof, and *Melaleuca alternifolia* oil.

WO 2016/051403 discloses an insect-repellant, fungicidal, bactericidal composite material for preservation of crops, the material including a non-woven fabric and a microencapsulated essential oil embedded in the non-woven fabric, wherein the microencapsulated essential oil can be selected among a huge number of essential oils, including lime, tea tree and oregano oils. The examples provided in the description envisage (example 1) the use of a fungicide (nefocide)+tea tree oil (or oregano oil)+rosemary oil or (example 2) the use of oregano oil (or tea tree oil)+rosemary oil. Effectiveness has been proven only for tea tree oil (example 8), mustard oil (example 8b) and oregano oil (example 8C).

US 2009/186096 discloses a method for the preparation of microencapsulated essential oils. Oregano and tea tree oils are mentioned among a high number of essential oils that can be used, together with possible additives, including i.a. vitamin E, for oral or topical application with a repelling action against insects and a bactericidal action. Lime oil is only mentioned among the essential oils that can be incapsulated as insect repellants or insecticides. This document is focused on the treatment of bovine mastitis, caused by bacterial infections.

Finally, U.S. Pat. No. 6,680,074 discloses a composition including propolis, oregano oil and at least one essential oil, for topical application and useful for treating microbial infections, including viral and mycotic infections. The above-mentioned essential oil can be i.a. *Melaleuca alternifolia* oil.

SUMMARY OF THE INVENTION

The problem underlying the present invention was that of providing a composition for the topical treatment of skin mycoses, containing active substances of natural origin, that presented a great tolerability and that was provided with an improved action with respect to that of the compositions of the prior art.

Such problem has been solved by providing a composition for topical application with antifungal activity containing *Melaleuca Alternifolia* essential oil, oregano essential oil, lime essential oil and a vitamin E ester.

By "vitamin E" it is meant tocopherol, in form of D-alpha-tocopherol as well as in form of mixture of the two enantiomers d and l of the alpha-tocopherol, or a mixture of other tocopherols (β, γ, δ, ε, ζ, η) or a tocotrienol.

By "vitamin E ester" it is meant a vitamin E ester as defined above with a carboxylic acid of formula R—COOH, wherein R is an alkyl radical having from 1 to 19 carbon atoms, or an alkenyl or alkynyl radical having from 2 to 19 carbon atoms.

Preferably, the aforementioned ester is vitamin E acetate, n-propionate or linoleate.

Particularly preferred is the use of vitamin E acetate, in particular alpha-tocopheryl acetate.

Preferably, the aforementioned essential oils of *Melaleuca Alternifolia*, oregano and lime constitute at least 3% by weight of the composition and each of them constitutes at least 1% by weight of the composition.

The composition according to the invention preferably contains from 10% to 97% of said vitamin E ester, which is preferably alpha-tocopheryl acetate.

According to an aspect of the present invention, the composition consists of *Melaleuca alternifolia* essential oil, oregano essential oil, lime essential oil and an ester of vitamin E, preferably alpha-tocopheryl acetate.

A particularly preferred composition consists of 95%-97% of alpha-tocopheryl-acetate and 3-5% of the aforementioned essential oils, each one of these essential oils constituting at least 1% by weight of the composition.

In another aspect of the present invention, the composition is formulated as a hydrophobic gel containing at least 3% of the aforementioned essential oils of *Melaleuca alternifolia*, oregano and lime, each one of such essential oils constituting at least 1% by weight of the composition, from 10% to 50% of a vitamin E ester, preferably alpha-tocopheryl-acetate, from 20% to 60% of a vegetable butter or wax, from 10% to 30% of triglyceride of caprylic and capric acid and from 5 to 20% of a gelling agent for lipids, such as, for example, the triglyceride of palmitic and stearic acid.

Such hydrophobic gel can further comprise one or more of hydrogenated castor oil, phytosterols and ceramide. Preferably, the vegetable butter is shea butter and the ceramide is ceramide-NP.

The composition according to the present invention, when topically applied on the skin, scalp and nails, exerts a powerful antifungal activity against a broad spectrum of fungi, including dermatophytes, yeasts and molds. The composition according to the present invention is particularly indicated for the treatment of onychomycoses.

As will be demonstrated by the experimental results provided in the detailed description of the invention, the three essential oils included in the composition according to the invention prove to act in a synergistic manner against several fungi responsible for various dermatomycoses.

The presence of a considerable quantity of a vitamin E ester in the composition according to the invention allows to prevent or counter possible irritating or allergizing effects that have sometimes been encountered during the topical application of the essential oils in question.

Indeed, as explained in the patent application WO 97/45098, esterified vitamin E, in particular vitamin E acetate, is spread rather easily, is absorbed surprisingly rapidly and, not being a molecule foreign to the human organism, it can easily integrate with the lipids present in the stratum corneum, exercising a considerable moisturizing and lenitive effect, useful to prevent or counter the potential irritating effects of the aforementioned oils.

Unlike the vitamin E used in its free form in the composition according to patent application US 2004/151710, the vitamin E esters, and in particular vitamin E acetate, do not perform any antioxidant action. Their contribution to the action of the composition according to the present invention is thus to be attributed to the aforementioned moisturizing and lenitive effects.

A similar preventing or countering effect towards the potential irritating or allergizing effects of the essential oils is obtained by formulating the composition according to the invention in form of a hydrophobic gel, as described above.

The term "hydrophobic" attributed to such formulations means that they do not contain water or other aqueous or polar solvent in any state, e.g. free or emulsified, comprising instead the hydrophobic substances indicated in the present invention.

The vegetal butter used in such formulations can be selected from those which are commonly available, such as: shea, cocoa, almond, kokum (Garcinia Indica), green tea, apricot, orange, lemon, pistachio, coffee etc. Shea butter is particularly preferred. The wax can be selected from those commonly available too; preferred waxes are rice wax and beeswax. The vegetal butter or wax is employed in a quantity comprised between 20 and 60%, preferably between 30 and 50%, for example between 35-45%.

The triglyceride of caprylic and capric acid is a synthetic triester of glycerin with C8-C10 acid—caprylic acid (C8) and capric acid (C10) deriving from the fractioning of coconut oil. It is colorless to slightly yellow, slightly viscous, odorless liquid. It is a valid substitute of the vegetable oils and with respect to the latter it is stable to oxidation because it is completely saturated. It has remarkable emollient qualities. This product is employed in the present formulations in a quantity comprised between 10 and 30%, preferably between 15 and 25%.

The gelling agent for lipids is preferably selected from the group comprising triglyceride of palmitic and stearic acid (INCI name: Palmitic/Stearic Triglyceride), Sorbitan Olivate, Dibutyl Lauroyl Glutamide, Dibutyl Ethylhexanoyl Glutamide, Magnesium/Aluminum/Hydroxide/Carbonate, Magnesium Hydroxide, Zinc Carbonate Hydroxide/Aluminum Hydroxide, Silica or methylcellulose polymers.

Preferred gelling agents are Sorbitan olivate, which additionally imparts a barrier effect, and the triglyceride of palmitic and stearic acid, that also has skin emollient and antioxidant properties, and the Silica; both Sorbitan Olivate and the triglyceride of palmitic and stearic acid are highly environmentally-friendly and stable to oxidation. Such products are commercially available from several sources, for example with the trademark Olifeel® (pearls) as far as the triglyceride of palmitic and stearic acid is concerned, and with the trade mark Olivem® 900 as far as Sorbitan Olivate is concerned. The gelling agent is employed in the formulations in a quantity comprised between 5 and 20%.

The present formulations can optionally contain a lower quantity of ceramide and/or phytosterols. Ceramide is a waxy lipid composed by sphingosine and fatty acids; it is typically present in the stratum corneum of the skin, where it prevents the phenomena of dehydration and increments its barrier function. Nine natural ceramides are known, and all of them are usable within the scope of the invention, on their own or mixed together. Particularly preferred is the ceramide-NP or ceramide-3, composed by non-hydroxylated N-acyl fatty acids and sphingosine.

Phytosterols are a group of vegetable steroids, with a structure similar to the one of cholesterol. Typical members of this class are stigmasterol, sitosterol, campesterol etc., which can be used individually or mixed together. Preferred compositions can comprise from 0.1 to 1% of ceramide (preferably from 0.01 to 0.4%) by weight on the weight of the composition. They can furthermore comprise from 0.1 to 2% of phytosterols by weight of the total weight of the composition.

Optionally, the formulations of the invention can include further ingredients, which may be either excipients or further active substances. Among the excipients, in particular, there are hydrogenated castor oil, preferably present in a percentage between 1 and 10%, more preferably between 0.1 and 6% by weight of the weight of the composition. Further excipients can be further hydrophobic components, preservatives, rheology modifiers, perfumes, etc. Further hydrophobic components are, for example, vegetable oils and fatty acid esters such as octyl palmitate, isopropyl myristate and ethyl oleate or their mixtures.

The hydrophobic gel according to the invention has an optimal stability, a great spreadability on the skin, and is absorbed with great rapidity, exercising a remarkable moisturizing and emollient effect, that is maintained for many hours after the application and is useful to prevent or counter the potential irritating effects of the aforementioned essential oils.

DETAILED DESCRIPTION

The present invention will be further described with reference to some exemplary embodiments provided for the purpose of illustration and not of limitation, wherein the indicated percentages are percentages by weight of the total weight of each composition.

Example 1

Alpha-tocopheryl acetate 97%
*Melaleuca Alternifolia* Oil 1%
Oregano Oil 1%
Lime Oil 1%

A composition according to the invention has been prepared with the aforementioned listed ingredients, by dispersing the three essential oils in the alpha-tocopheryl acetate under stirring at room temperature, until an oily, limpid and viscous fluid is obtained.

Example 2

Alpha-tocopheryl acetate 96%
*Melaleuca Alternifolia* Oil 2%
Oregano Oil 1%
Lime Oil 1%

This composition was prepared in the same way as illustrated in Example 1.

Example 3

Shea butter 38%
Alpha-tocopheryl acetate 30%
Triglyceride of caprylic and capric acid 19%
Triglyceride of palmitic and stearic acid 7%
Hydrogenated castor oil 2.3%
*Melaleuca Alternifolia* oil 1%
Oregano oil 1%
Lime oil 1%
Phytosterols 0.4%
Ceramide-NP 0.3%

A hydrophobic gel was prepared with the aforementioned ingredients in the following manner: it is prepared a first phase comprising alpha-tocopheryl acetate, hydrogenated castor oil, phytosterols, ceramides, heating all until 120° C. to obtain a homogeneous solution. In a separate container the missing ingredients are heated up to 60° C. The two phases are then joined and mixed together for about 30 minutes at room temperature.

The antifungal activity of the composition according to the present invention was tested using the formulation of example 1 in comparison with similar formulations with a different content of essential oils.

In particular, the compositions provided in the following table 1 have been compared:

TABLE 1

| Composition | Example 1 | Comparison 1 | Comparison 2 | Comparison 3 |
|---|---|---|---|---|
| Alpha-tocopheryl acetate | 97 | 97 | 97 | 97 |
| Melaleuca Alternifolia oil | 1 | — | 1.5 | 3 |
| Oregano oil | 1 | — | — | — |
| Lime oil | 1 | 3 | 1.5 | — |

The inhibitory activity of each of the four compositions listed above against dermatophytes, which are cause of skin mycoses, has been evaluated on the basis of in vitro studies.

Such evaluation has been performed by means of the following two methods:

Method 1: agar diffusion method or MIC (Minimal Inhibitory Concentration) sensitivity test.

It is a quantitative method for evaluating the sensitivity of dermatophytes strains towards substances with an inhibiting activity towards their growth or with an antimicrobial activity in vitro.

The following strains of microorganisms have been used:
Dermatophyte: ATCC
*Trichophyton mentagrophytes* 9533
*Trichophyton* Rubrum 18753
*Fusarium* species 3636
*Candida albicans* 10231
*Aspergillus brasiliensis* 16404

The microorganisms listed above were cultured on plates containing as growth medium "Sabouraud's dextrose Agar" with cycloheximide, chloramphenicol and gentamicin.

Discs of nitrocellulose with a diameter of 1.0 cm were put into contact with each one of the compositions of Table 1, until complete imbibition of the disc.

Such discs were then placed, sufficiently spaced from each other, on plates containing the aforementioned microorganisms.

The plates containing *Trichophyton mentagrophytes* and *Trichophyton Rubrum* were then incubated at 25° C. for 15 days, those containing *Fusarium* species for 10 days at 25° C., those containing *Candida albicans* for 5 days at 25° C. and those containing *Aspergillus brasiliensis* for 7 days at 25° C.

After the end of the period of incubation at 25° C., the diameter of the inhibition halo formed around each disc was measured.

The sensitivity of each microorganism to the tested composition is established on the basis of the measure of the diameter of the inhibition halo, attributing the following evaluations:

R (resistant), when the diameter is null (there is no inhibition halo);

L (light), when the diameter is small; light sensitivity of the microorganism;

M (medium), when the diameter is medium; medium sensitivity of the microorganism;

S (strong), when the diameter is large; the microorganism is very sensitive.

The results obtained by this experimentation are reported in the following Table 2.

TABLE 2

| Microorganism | Example 1 | Comparison 1 | Comparison 2 | Comparison 3 |
|---|---|---|---|---|
| Trichophyton mentagrophytes | S | L | S | S |
| Trichophyton Rubrum | M | L | M | M |
| Fusarium species | M | M | M | M |
| Candida albicans | S | S | M | S |
| Aspergillus brasiliensis | S | S | M | S |

Method 2: Suspension Method

With this method, the ability or inability of a microorganism to multiply in vitro in the presence of a given concentration of a substance with an antimicrobial activity was evaluated.

Respective suspensions of the aforementioned microorganisms were prepared in a liquid growth medium, constituted by "Sabouraud's dextrose broth" with cycloheximide, chloramphenicol and gentamicin. Such suspensions contained a known quantity of microorganisms, expressed in Colony Forming Units per ml (CFU/ml), in the order of $10^5$.

Within a tube, 9 g of test formulation were put into contact with 1 ml of suspension with a known concentration of each microorganism.

After a contact time of 1 hour at 37° C., the total microbial count was determined by inclusion of 1 ml of a sample in duplicate in a plate of the serial dilution. The result was expressed in CFU/ml.

The results are summarized in the following Table 3:

TABLE 3

| microorganism | Initial inoculum (CFU/ml) | Example 1 (CFU/ml) | Comparison 1 (CFU/ml) | Comparison 2 (CFU/ml) | Comparison 3 (CFU/ml) |
|---|---|---|---|---|---|
| Trichophyton mentagrophytes | $1.80 \cdot 10^5$ | $4.0 \cdot 10^3$ | $1.0 \cdot 10^5$ | $3.0 \cdot 10^4$ | $1.0 \cdot 10^4$ |
| TrichophytonRubrum | $1.80 \cdot 10^5$ | $2.0 \cdot 10^4$ | $9.0 \cdot 10^4$ | $6.0 \cdot 10^4$ | $2.8 \cdot 10^4$ |
| Fusarium species | $1.90 \cdot 10^5$ | $8.0 \cdot 10^3$ | $1.0 \cdot 10^5$ | $2.9 \cdot 10^4$ | $1.8 \cdot 10^4$ |
| Candida albicans | $2.30 \cdot 10^5$ | $1.0 \cdot 10^3$ | $5.0 \cdot 10^3$ | $2.2 \cdot 10^3$ | $1.0 \cdot 10^3$ |
| Aspergillus brasiliensis | $1.00 \cdot 10^5$ | $1.2 \cdot 10^3$ | $1.0 \cdot 10^3$ | $7.0 \cdot 10^3$ | $1.0 \cdot 10^3$ |

On the basis of such results it is possible to calculate the microbial reduction obtained with the different formulations, expressed in percentages with respect to the initial microbial count. The values of microbial reduction calculated this way are reported in the following table 4.

TABLE 4

| | Microbial reduction (%) | | | |
|---|---|---|---|---|
| microorganism | Example 1 | Comparison 1 | Comparison 2 | Comparison 3 |
| Trichophyton mentagrophytes | 97.78% | 44.44% | 83.33% | 94.44% |
| Trichophyton Rubrum | 88.89% | 50.00% | 66.67% | 84.44% |
| Fusarium species | 95.79% | 47.37% | 84.74% | 90.53% |
| Candida albicans | 99.57% | 97.83% | 99.04% | 99.57% |
| Aspergillus brasiliensis | 98.80% | 99.00% | 93.00 | 99.00 |

It is noted from Table 4 that the composition according to Example 1 brings about a significantly greater microbial reduction than that caused by the comparison compositions for the first three microorganisms used in the test and a microbial reduction substantially equivalent to that determined by Comparison 3 (*Melaleuca alternifolia* Oil 3%, alpha-tocopheryl acetate 97%) for *Candida albicans* and *Aspergillus brasiliensis*.

This result is completely unexpected, because the composition according to Example 1 differs from that according to Comparison 3 in that it contains only 1% of *Melaleuca alternifolia* oil instead of 3% and in that it contains, in addition to 1% of oregano oil, 1% of lime essential oil, which in the composition of Comparison 2 (1.5% lime oil, 1.5% *Melaleuca alternifolia* oil, 97% alpha-tocopheryl acetate) has instead caused a clear decrease in microbial reduction with respect to that achieved with the composition of Comparison 3.

Due to the superiority demonstrated by the composition according to Example 1 in the aforementioned comparative tests, the activity spectrum of this composition was further investigated.

Method 2 described above was repeated using other microorganisms which are responsible for cutaneous fungal infections and the results of the following Table 5 were obtained:

TABLE 5

| Microorganism | Initial inoculum (CFU/ml) | Example 1 (CFU/ml) | Microbial reduction (%) |
|---|---|---|---|
| *Scopulariopsis brevicaulis* ATCC 62614 | $1.60 \cdot 10^5$ | $5.5 \cdot 10^4$ | 65.63% |
| *Epidermophyton floccosum* ATCC 28188 | $1.30 \cdot 10^5$ | $1.4 \cdot 10^4$ | 89.23% |
| *Acremonium* species ATCC 90507 | $1.80 \cdot 10^5$ | $1.8 \cdot 10^4$ | 90.00% |
| *Penicillium* species ATCC 10106 | $1.80 \cdot 10^5$ | $1.0 \cdot 10^4$ | 94.44% |

As it can be seen from Tables 4 and 5, the composition according to Example 1 has been shown to be effective against a wide spectrum of microorganisms susceptible to causing skin fungal infections. Consequently, the composition according to the present invention can be used for the treatment of mycoses on skin, scalp and nails without the need for preventive diagnostic investigations aimed at identifying the microorganism or microorganisms involved.

Furthermore, being based on substances of natural origin such as the essential oils of *Melaleuca alternifolia*, oregano and lime, it is substantially devoid of toxicity. The presence of a substantial amount of vitamin E esters also prevents or at least mitigates any irritating or allergenic effects due to the essential oils.

From some preliminary tests carried out with the composition according to Example 3 on the microorganisms shown in Table 4, microbial reduction effects similar to those obtained with the composition according to Example 1 were found.

The invention claimed is:

1. A topical anti-fungal composition consisting essentially of therapeutically effective amounts of *melaleuca alternifolia* essential oil, oregano essential oil, lime essential oil and a component selected from the group consisting of vitamin E acetate, n-propionate and linoleate.

2. The composition of claim 1, wherein the total of said essential oils of *Melaleuca alternifolia*, oregano and lime constitute at least 3% by weight of the total composition and each of them individually constitutes at least 1% by weight of the total composition.

3. The composition of claim 2, containing from 10% to 97% of said component in the total composition.

4. The composition of claim 3, wherein said component is alpha-tocopheryl acetate.

5. The composition of claim 3, consisting of *Melaleuca alternifolia* essential oil, oregano essential oil, lime essential oil and said component.

6. The composition of claim according to claim 5, consisting of 95%-97% alpha-tocopheryl acetate and 3-5% of said essential oils, each one of said essential oils constituting at least 1% by weight on the weight of the total composition.

7. The composition of claim 2, in the form of hydrophobic gel, containing 10 to 50% of said component, 20 to 60% of a vegetable butter or wax, from 10 to 30% triglyceride of caprylic and capric acid and from 5 to 20% of a gelling agent selected from the group consisting of triglyceride of palmitic and stearic acid, Sorbitan Olivate and Silica.

8. The composition of claim 7, further consisting of one or more of hydrogenated castor oil, phytosterols and ceramide.

9. The composition of claim 8, wherein said component is alpha-tocopheryl acetate, said vegetable butter is shea butter and said ceramide is ceramide-NP.

10. The composition of claim 1, wherein said component is alpha-tocopheryl acetate.

11. The composition according to claim 5, wherein said component is alpha-tocopheryl acetate.

* * * * *